United States Patent [19]
Shaw et al.

[11] Patent Number: 4,764,797
[45] Date of Patent: Aug. 16, 1988

[54] CHEMICAL-SENSITIVE SEMICONDUCTOR DEVICE

[75] Inventors: John E. A. Shaw, West Drayton; Alastair Sibbald, Maidenhead, both of England

[73] Assignee: Thorn Emi plc, London, England

[21] Appl. No.: 883,158

[22] Filed: Jul. 8, 1986

[30] Foreign Application Priority Data

Sep. 14, 1985 [GB] United Kingdom ............... 8522785

[51] Int. Cl.$^4$ .......................................... H01L 29/66
[52] U.S. Cl. ...................................... 357/25; 357/55
[58] Field of Search ..................... 357/25, 55, 23.5

[56] References Cited

U.S. PATENT DOCUMENTS

| | | | |
|---|---|---|---|
| 4,103,227 | 7/1978 | Zemel | 357/25 X |
| 4,508,613 | 4/1985 | Busta et al. | 357/25 X |
| 4,597,002 | 6/1986 | Anthony | 357/25 |
| 4,609,932 | 9/1986 | Anthony | 357/25 |
| 4,612,465 | 9/1986 | Schutten et al. | 357/23.4 X |
| 4,660,063 | 4/1987 | Anthony | 357/25 |

FOREIGN PATENT DOCUMENTS 2096824 10/1982 United Kingdom .

OTHER PUBLICATIONS

Moss, S. D., et al., "Hydrogen, Calcium, and Potassium Ion-Sensitive FET Transducers . . . ", IEEE Trans. on Biomedical Engr., Jan. 1978, pp. 49-54.

A. Sibbald et al., A Miniature Flow-Through Cell With a Four-Function Chemfet Integrated Circuit for Simultaneous Measurements of Potassium, Hydrogen, Calcium and Sodium Ions in *Analytica Chimica Acta*, vol. 159, 1984, pp. 47-62.

Ching-Chang Wen et al., Gate-Controlled Diodes for Ionic Concentration Measurement in *IEEE Transactions on Electron Devices*, vol. ED-26, No. 12, Dec. 1979, pp. 1945-1951.

Primary Examiner—Andrew J. James
Assistant Examiner—Sara W. Crane
Attorney, Agent, or Firm—Fleit, Jacobson, Cohn & Price

[57] ABSTRACT

A chemical-sensitive semiconductor device in the form of a chemical-sensitive field effect transistor, suitable for testing relatively small volumes of a fluid analyte, comprises a substrate provided with a passageway, interconnecting its major surfaces, along which the analyte can pass. Drain and source regions are formed at opposite ends of the passageway and a chemical-sensitive gate region is formed on the sides of the passageway.

12 Claims, 7 Drawing Sheets

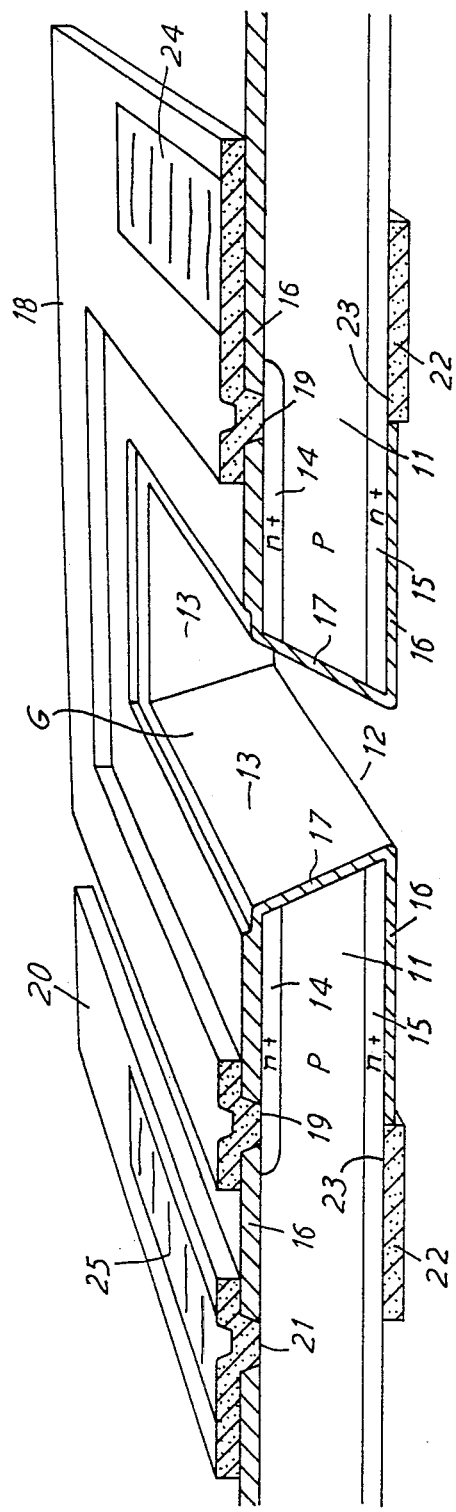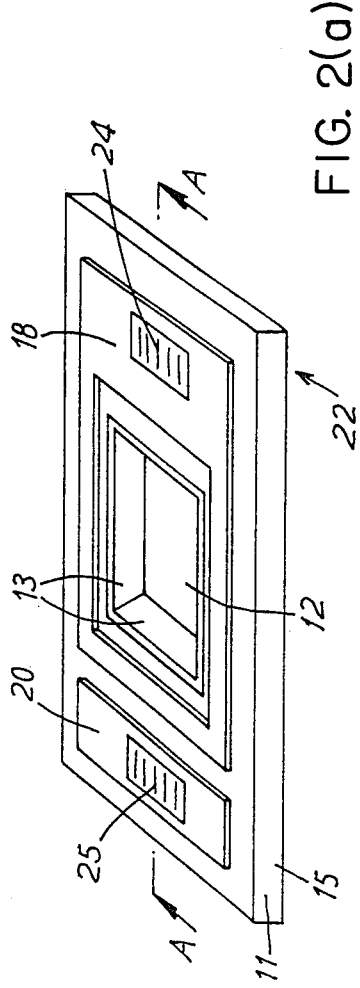
FIG. 2(b)
FIG. 2(a)

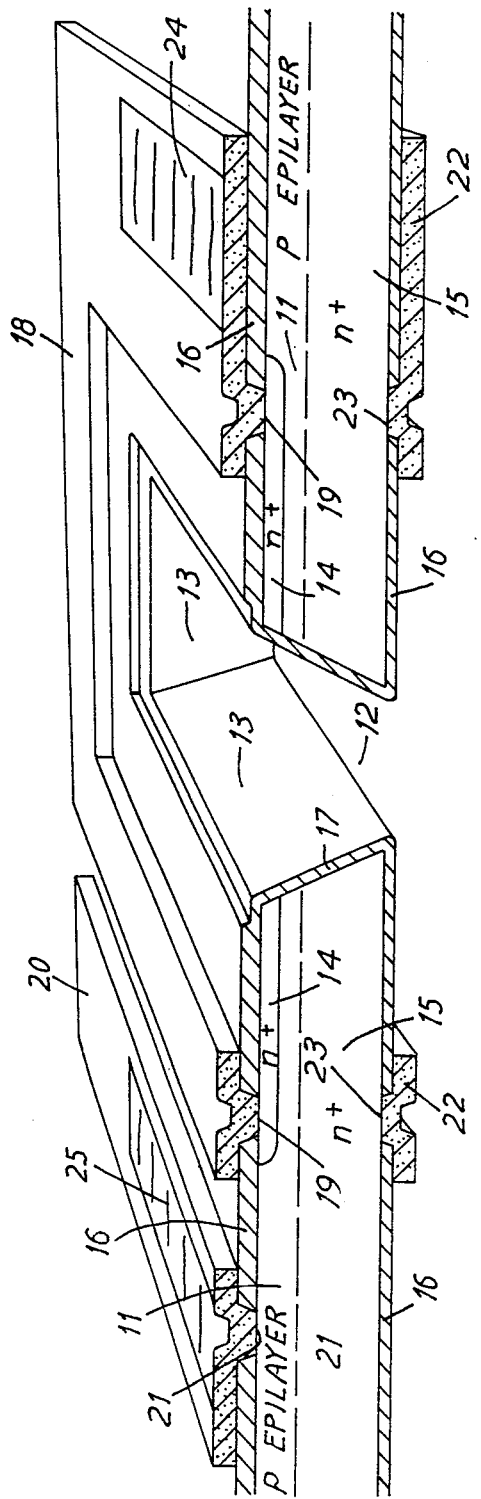
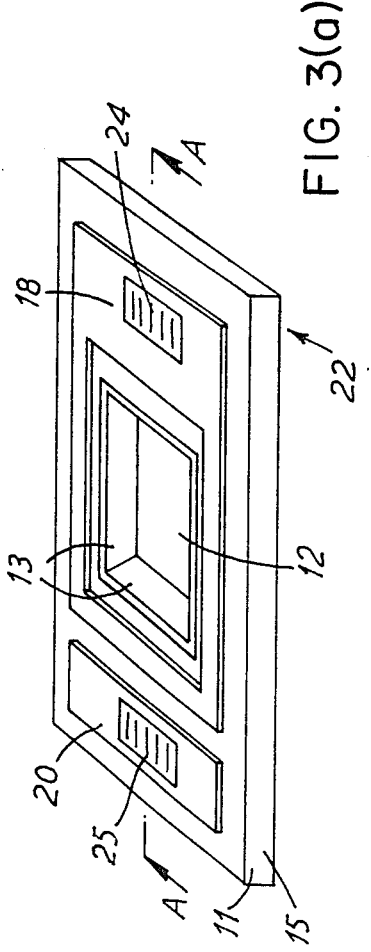
FIG. 3(b)
FIG. 3(a)

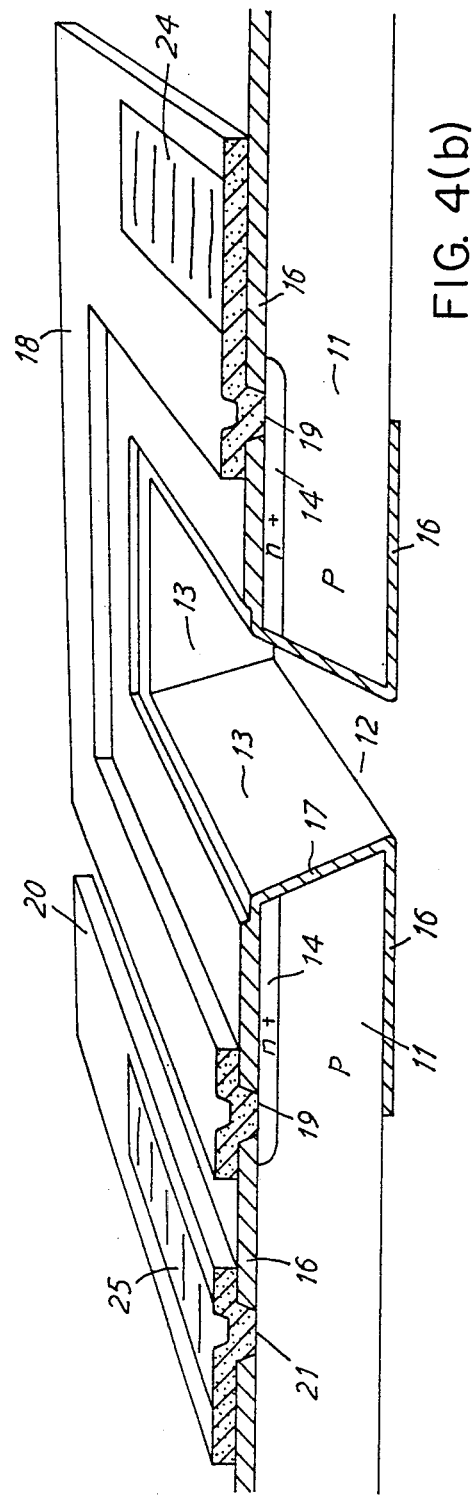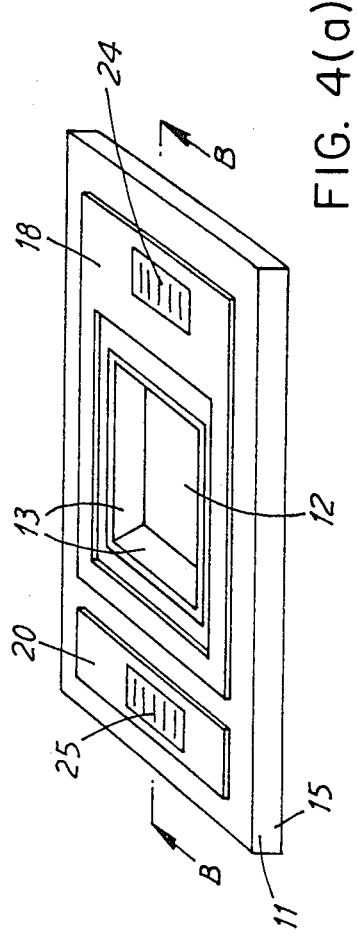
FIG. 4(b)
FIG. 4(a)

CHEMICAL-SENSITIVE SEMICONDUCTOR DEVICE

This invention relates to a chemical-sensitive semiconductor device and it relates particularly, though not exclusively, to a chemical-sensitive field effect transistor.

Figure 1:
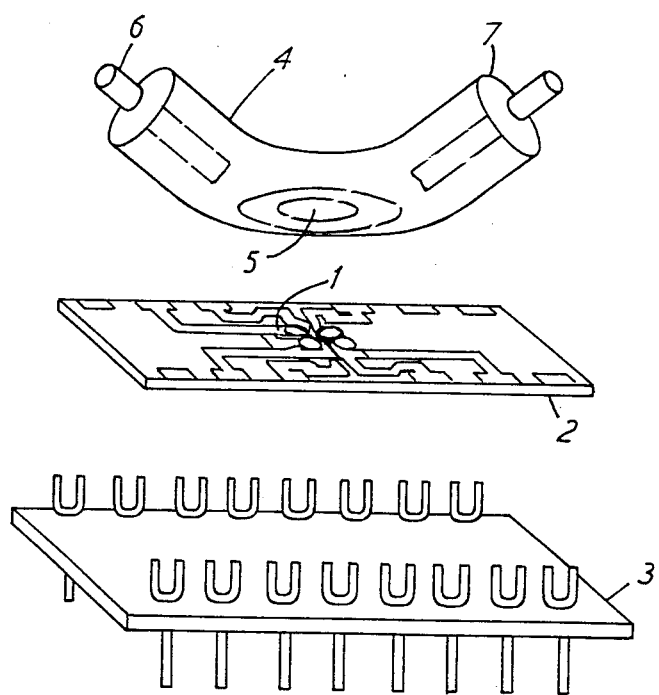

A chemical-sensitive semiconductor device suitable for the simultaneous measurement of potassium, hydrogen, calcium and sodium ions in aqueous solution—as in a blood sample, for example—has been described by A. Sibbald, P. D. Whalley and A. K. Covington in Analytica Chimica Acta Vol 159 1985 p47-62. This device, which is illustrated in FIG. 1 of the accompanying drawings, includes an integrated circuit 1 comprising four chemical-sensitive field effect transistors each having an exposed chemical sensitive gate region responsive to a respective one of the four ions under test. The integrated circuit is formed on a suitable substrate 2 which is mounted on a 16-pin DIL socket adapter 3.

An analyte is supplied to the gate regions along a bent glass tube 4 which is seated on the substrate and apertured at 5 to allow the sample to flow across the integrated circuit in contact with the four chemical sensitive gate regions.

A system of this kind has a flow-through volume typically of about 30 $\mu$l; however, in some applications (e.g. neo-natal blood tests) this may be unsatisfactory as only very small samples are available. Furthermore, there is a tendency for the samples to form a stagnant layer immediately above the gate regions so that at the conclusion of each test the system must be flushed out thoroughly and, in some applications, a volume as large as 500 $\mu$l may be needed.

It is an object of the present invention to provide a chemical sensitive semiconductor device which alleviates at least some of the problems associated with a device of the kind described hereinbefore.

Accordingly there is provided a chemical-sensitive semiconductor device comprising a substrate of a semiconductor material, a passageway interconnecting major surfaces of the substrate along which a sample under test may pass and a chemical-sensitive gate region formed on a wall of the passageway.

The present invention may be especially beneficial in that it is possible, with a construction of the kind defined, to fabricate a device having a relatively small flow-through volume. This may be of advantage in applications wherein only a relatively small sample is available—as would be the case in the testing of neo-natal blood samples.

It can be of advantage if the passageway is tapered-in the form, for example, of a truncated square-based pyramid. A configuration of this kind leads to improved contact between the analyte and the chemical-sensitive gate region and may be flushed out more readily at the conclusion of a test. In addition, a tapered configuration assists in the deposition of a chemical-sensitive layer and/or gate electrode.

Figure 5:
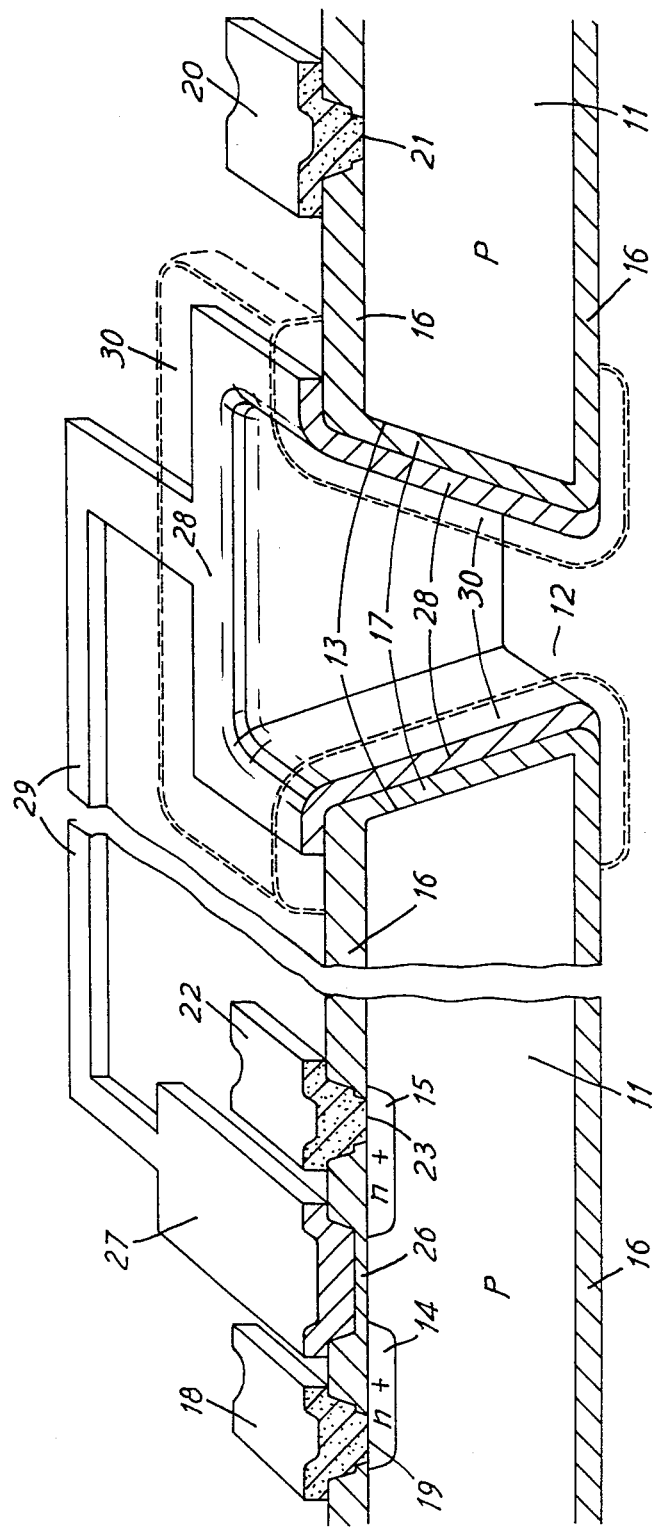
Figure 6A:
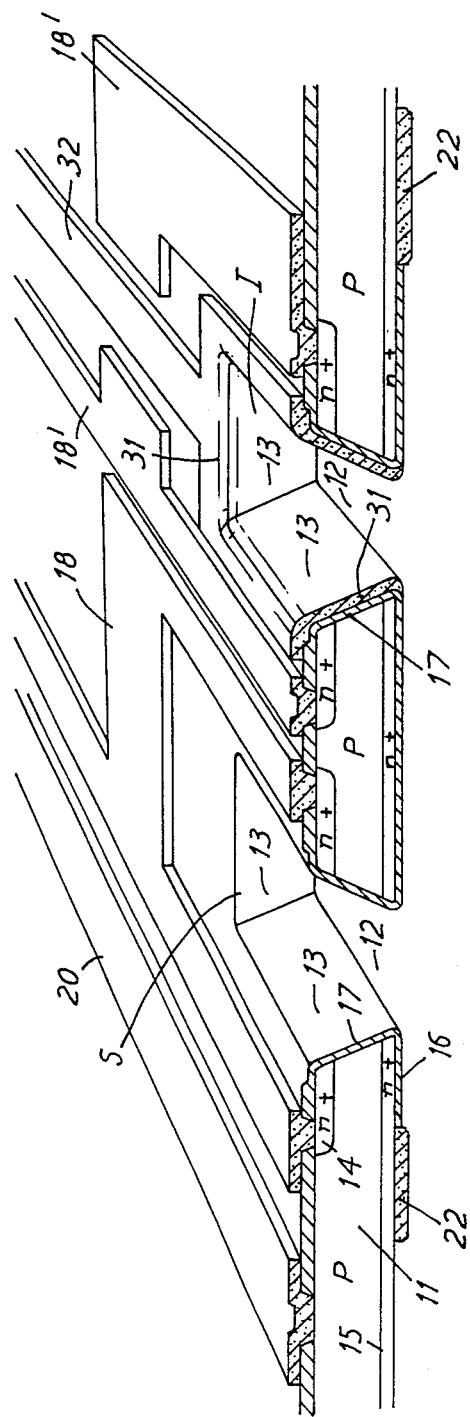
Figure 6B:
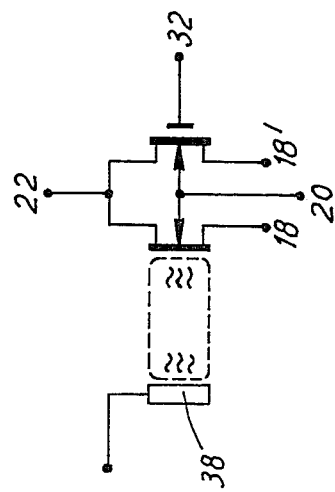
Figure 7:
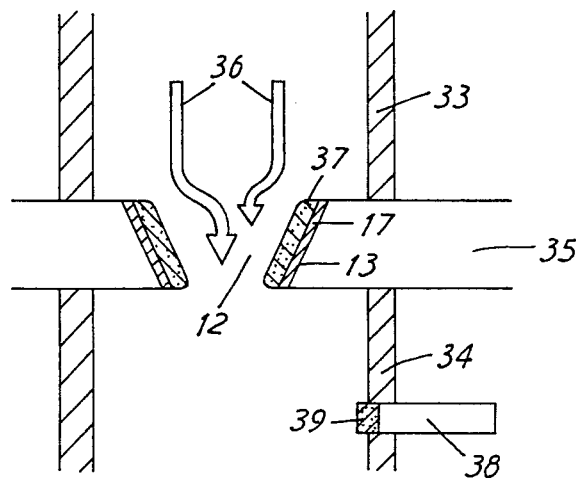
Figure 8:
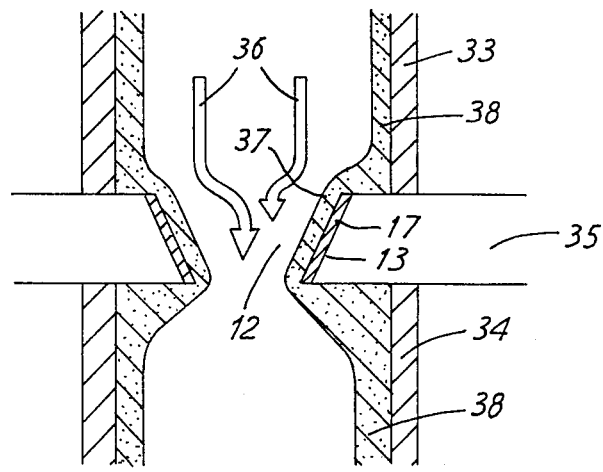

In order that the invention may be carried readily into effect different embodiments thereof are now described, by way of example only, by reference to the Figures of the drawings of which:

FIG. 1 shows a prior art device as described above,

FIG. 2a shows a perspective view of a chemical-sensitive field effect transistor in accordance with the present invention and FIG. 2b shows a sectional view taken on line A—A through the device shown in FIG. 2a, FIGS. 3a and 3b show a similar perspective view of, and a sectional view through, another example of a chemical sensitive field effect transistor in accordance with the present invention, FIG. 4a shows a perspective view of a chemical sensitive gate controlled diode in accordance with the present invention and FIG. 4b shows a sectional view taken on line B—B through the device shown in FIG. 4a, FIG. 5 shows a sectional view through a chemical sensitive field effect transistor in accordance with the present invention and provided with an extended gate electrode, FIGS. 6a and 6b show a sectional view through a dual FET device, FIG. 7 shows an arrangement for feeding an analyte through the passageway formed in a device in accordance with the invention and, FIG. 8 illustrates an extended chemically-sensitive layer.

Referring initially to FIG. 2 of the accompanying drawings, the device shown comprises a substrate 11 in the form of a (100) wafer of p-type crystalline silicon and a passageway 12, formed by a conventional V-MOS technique, interconnects the major surfaces of the wafer.

In this embodiment of the invention, the device incorporates a chemical-sensitive field effect transistor. To this end, source and drain regions 14, 15 of n+ type semiconductor material are formed around the passageway, at opposite ends thereof, and a chemical-sensitive gate region, referenced generally at G, is formed in the sides 13 of the passageway between the drain and source regions.

As is conventional in the art insulative layers 16 of silicon dioxide and, if desired, silicon nitride, are provided on the major surfaces of the wafer and a relatively thin layer 17, forming the gate insulator, is provided on the sides of the passageway. In addition an insulative guard layer (not shown) may be implanted around the source region 14 to inhibit leakage currents.

Electrodes 18, 20 and 22 form an electrical connection, respectively to the source, bulk and drain regions, via suitable openings 19, 21 on the oxide layers. Each electrode has a bond pad (e.g. 24, 25) to which a suitable lead may be attached. Apart from the chemical-sensitive gate region G and the bond pads which remain exposed the entire device is encapsulated in a thin protective film (not shown) of a polyimide material.

In use of the device an analyte under test is passed through the passageway so as to come into intimate contact with the chemical-sensitive gate region. As will be described in greater detail hereinafter the gate region can be fabricated to suit a desired application and, to this end, a suitable chemical-sensitive layer and/or gate electrode may be deposited on the oxide layer 17 covering the sides of the passageway. Examples of specific materials used are described hereinafter.

In this example, passageway 12 is tapered and is generally in the form of a truncated, square-based pyramid, as shown. This configuration is found to be particularly beneficial in that analyte passing through the passageway makes closer contact with the chemical-sensitive gate region and may be flushed out more readily at the conclusion of a test. In addition, this tapered configuration assists in the deposition of a chemical-sensitive layer and/or gate electrode.

By using a conventional V-MOS etch technique the size of the passageway can be controlled accurately by limiting the area exposed to the etchant. The etchant normally used is potassium hydroxide which selectively etches the (100), but not the (111), faces. In these circumstances, the sides of the passageway are formed by the (111) faces and the truncated square-based pyramid configuration results.

Typically, a passageway as small as 1-2 mm square at the inlet side, 0.4-1.4 mm square at the outlet side and 0.4 mm deep can be achieved, although clearly alternative dimensions are possible. In the case of a passageway 1.2 mm square at the inlet side, 0.6 mm square at the outlet side and 0.375 mm deep the flow-through volume is about 0.32 $\mu$l. It will be appreciated that this volume is significantly smaller than the corresponding volume, typically 30 $\mu$l, obtained using a hithertoknown design of the kind already described. In practice, it is possible using a device in accordance with the present invention to successfully conclude a test using a sample volume as small as 2 $\mu$l, as compared with a much larger sample volume, typically 500 $\mu$l, needed using a prior design. It will be appreciated, therefore, that the present invention may be of considerable benefit particularly when only very small samples are available, when testing neo-natal blood samples, for example.

It will be appreciated that passageway 12 need not necessary have a truncated, pyramidal configuration, as described. Alternatively, for example, the hole could have a conical formation, as produced using an appropriate non-selective etchant, such as a mixture of hydrofluoric and nitric acids.

It will further be appreciated that the substrate could alternatively be of a n+ type semiconductor material, the drain and source regions being of a p-type material.

FIGS. 3 show an alternative embodiment in which the FET is formed by using conventional epitaxial layer techniques. In this case an n+ type substrate forms the drain region 15 and comprises crystalline silicon oriented so that the major surfaces are (100) faces. Again, a region is etched to form a truncated pyramidal passageway 12 having four (111) oriented faces 13. A bulk region 11 comprises an epitaxial p-type layer deposited on one side of the n+ type substrate. The source region comprises an n+ region 14 formed on the epitaxial p-type layer round the passageway 12. A thin implanted insulating layer around the source region 14, together with oxide/nitride layers 16 and 17, conductors 18, 20 and 22, contact regions 19, 21 and 23, and bond pads 24 and 25 are as described hereinbefore in relation to the embodiment of FIG. 2.

FIG. 4 shows another embodiment in accordance with the present invention.

The construction is similar to that of FIG. 2, except that the device incorporates a gate controlled diode instead of a field effect transistor; in this example, connector 20 becomes the anode of the device, connector 18 becomes the cathode, the connector shown at 22 in FIG. 2 together with the drain region shown at 15 being omitted. Details of the operation of ion sensitive gate controlled diodes are described in a paper "Gate Controlled Diodes for Ionic Concentration Measurement" by Chen & Zemel (IEEE Transactions on Electron Devices, Vol ED-26, No. 12, Dec. 1979, pp. 1945-1951).

As disclosed in UK Patent Application No. 2096824A, extension of the gate of a chemical-sensitive FET enables the chemical-sensitive region to be positioned remotely from the FET and results in simplified encapsulation and improved long-term electrical stability. An embodiment of the present invention incorporating an extended gate FET is shown in FIG. 5. Compared with FIG. 2, the FET is located remotely from passageway 12, the source and drain regions 14 and 15 respectively being in close proximity on the same side of the p-type substrate 11. The source and drain conductors are shown at 18 and 22 in FIG. 5. Between regions 14 and 15, a silicon oxide/nitride layer 26 is relatively thin and forms the gate insulator on which the gate electrode 27 is formed. A conducting layer 28 is formed on the sides 13 of passageway 12. The gate conductor 27 and the conducting layer 28 are joined by the deposited conducting strip 29 to form an extended gate remote from the FET. In this example, a chemical-sensitive layer 30 is deposited to cover the conducting layer 28 completely.

In some applications it is desirable to compensate for the effect of temperature and light on the sensitivity of a chemical sensitive device. A convenient way of providing such compensation is to use a matched pair of devices, one device being chemically sensitive and exposed to the analyte fluid, the other device having the same geometry but being insensitive to the analyte under test.

An example in accordance with this invention is shown in FIG. 6a in which one device, referenced at S, is sensitive to the analyte and is constructed as described by reference to FIG. 2 and the other device, referenced at I, is insensitive to the analyte and has an electrode 31 deposited on the sides 13 of the passageway 12. Connection to the electrode 31 is made via the deposited conductor 32. FIG. 6b shows the electrical connections to the matched devices together with a reference electrode 38 for device S. An arrangement for feeding the analyte fluid through passageway 12 is shown in FIG. 7. Tubes 33 and 34 are attached to either side of the chemical-sensitive gate controlled semiconductor device 35 with the passageway 12 within the bore formed by the tubes. As shown by arrows 36, the analyte fluid is arranged to flow in the direction in which the passageway becomes smaller. This ensures good contact with chemical-sensitive layer 37 deposited on the gate insulator 17 formed on the sides 13 of the passageway.

A reference electrode 38 having a porous plug 39 can conveniently be inserted into the exit tube 34 so that the porous plug 39 is in contact with the analyte.

Multiple sensing can be achieved by forming different chemical-sensitive layers in different regions of the wall of the passageway and providing an independent semiconductor device for each different sensitive layer. Alternatively or in addition the analyte could flow through more than one device having a tapered hole.

By a suitable choice of a chemical-sensitive layer and/or gate electrode deposited on the sides of passageway 12 it is possible to fabricate a wide range of different chemical-sensitive devices in accordance with the invention. Examples only of different materials which could be used include inorganic oxides or nitrides such as $Si_3N_4$ (i.e. layer 17), $Al_2O_3$, $ZrO_2$ or $Ta_2O_5$ which are used in conjunction with a reference electrode (e.g. electrode 38 in FIG. 7) and are sensitive to $H^+$ ions.

A gate electrode formed as a metallisation of platinum and/or palladium on oxide layer 17 and sensitive to H₂ or hydrogen containing gases (e.g. NH₃, H₂S).

Glasses deposited on layer 17 used in conjunction with a reference electrode and sensitive to specific cations (e.g. $H^+$, $Na^+$, $K^+$).

Porous palladium deposited as a gate electrode on oxide layer 17 and sensitive to CO.

In addition, chemical-sensitive layers can be formed on the oxide layer by solvent casting. The chemical sensitive material is dissolved or suspended in a plasticized polymer, silicone rubber or a similar inert support matrix known to those skilled in the art. A suitable plasticized polymer comprises polyvinyl chloride (PVC) powder dissolved in tetrahydrobafuran with dioctylsebacate added. The viscous solution is either coated on gate insulator 17 to form the chemical-sensitive layer or it is passed through the entrance tube 33, the passageway 12 and the exit tube 34 to form a deposit 37 on the gate insulator 17 together with deposits 38 on the surfaces of the tubes 33, 34, as shown in FIG. 8. This is particularly advantageous if the deposit adheres better to the tubes than to the passageway surfaces.

Examples of suitable chemical-sensitive materials include,

Anion exchangers e.g. calcium dialkylphosphate in dioctylphenylphosphate, sensitive to $C_a^+$ ions;

Ionophores, e.g. valinomycin, sensitive to $K^+$ ions;

Sparingly soluble, non-porous particles of salts, e.g. LaF₃, sensitive to $F^-$ ions; AgCl/AgBr/AgI, each sensitive to Cl/Br/I ions;

Enzyme substrates immoblised in a gel and coated on to an $H^+$ sensitive gate (e.g. silicon nitride), e.g. penicillinase, sensitive to penicillin;—glucose dehydrogenase, sensitive to glucose.

A further example of a chemical sensitive layer is formed by coating the gate insulator 17 with a hydrophilic gel and then depositing by sputtering a gate electrode in the form of a porous gold film. This arrangement enables water vapour to be detected. A suitable hydrophilic gel is polymerized polyvinyl chloride alcohol (PVA), which can be prepared in the same way as the plasticized hydrophobic PVC described hereinbefore.

It will be appreciated that the present invention provides a chemical-sensitive semiconductor device suitable for testing relatively small fluid smaples. It will be appreciated by those skilled in the art that the device may be fabricated to detect, and/or measure concentration of, a wide range gases, vapours and ions in solution.

We claim:

1. A chemical-sensitive semiconductor device comprising a substrate of a semiconductor material, a passageway interconnecting major surfaces of the substrate along which a sample under test may pass and a chemical-sensitive gate region formed on a wall of the passageway and wherein said passageway is tapered.

2. A device according to claim 1 wherein said passageway is in the form of a truncated, square-based pyramid.

3. A device according to claim 1 or claim 2 in the form of a chemical-sensitive field effect transistor having a drain region and a source region.

4. A device according to claim 3 wherein the drain region and the source region are at opposite ends of the passageway.

5. A device according to claim 3 wherein the drain and source regions of the transistor are of one polarity type and one of the drain region and the source region is formed in an epitaxial layer of the opposite polarity type.

6. A device according to claim 3 wherein the drain and source regions of the transistor are remote from the chemical-sensitive gate region and are coupled thereto by an extended gate conductor.

7. A device according to claim 1 including a first field effect transistor having a first said tapered passageway provided with a first chemical-sensitive gate region and a second field effect transistor having a second said tapered passageway provided with a second chemical-sensitive gate region, wherein one only of the first and second chemical-sensitive gate regions is sensitive to a particular analyte and both of the gate regions have substantially the same sensitivity to the influence of light and temperature, the first and second field effect transistors being coupled together to be capable of producing an output signal representing said particular analyte only.

8. A device according to claim 1 or claim 2 in the form of a chemical-sensitive gate controlled diode.

9. A device according to claim 1 including a duct arranged to convey analyte to, and away from, said passageway.

10. A device according to claim 3 including a reference electrode mounted in a wall of said duct.

11. A device according to claim 9 wherein said chemical-sensitive gate region includes a layer of a chemical-sensitive material, said material being deposited also on an inner surface of the duct.

12. A device according to claim 10 or claim 11 wherein said reference electrode includes a porous plug which, in use, is exposed to analyte passing along said duct.

* * * * *